(12) United States Patent
Houghton et al.

(10) Patent No.: US 8,012,505 B2
(45) Date of Patent: Sep. 6, 2011

(54) DOSAGE FORM HAVING A SACCHARIDE MATRIX

(75) Inventors: Christian Gauguin Houghton, Gentofte (DK); Annette Römmelmayer Lundegaard, Søborg (DK)

(73) Assignee: Alk-Abello A/S, Horsholm (DK)

(*) Notice: Subject to any disclaimer, the term of this patent is extended or adjusted under 35 U.S.C. 154(b) by 829 days.

(21) Appl. No.: 10/785,698

(22) Filed: Feb. 23, 2004

(65) Prior Publication Data

US 2004/0228919 A1 Nov. 18, 2004

Related U.S. Application Data

(60) Provisional application No. 60/465,383, filed on Apr. 25, 2003.

(30) Foreign Application Priority Data

Feb. 28, 2003 (DK) .................................. 2003 00318

(51) Int. Cl.
*A61K 9/14* (2006.01)
(52) U.S. Cl. ....................................................... 424/484
(58) Field of Classification Search .................... 424/484
See application file for complete search history.

(56) References Cited

U.S. PATENT DOCUMENTS

| | | | |
|---|---|---|---|
| 4,371,513 A | 2/1983 | Sanchez | |
| 4,371,516 A | 2/1983 | Gregory et al. | |
| 4,698,264 A * | 10/1987 | Steinke | 428/402.2 |
| 5,244,663 A | 9/1993 | Bruttmann et al. | |
| 5,343,672 A | 9/1994 | Kearney et al. | |
| 5,648,093 A | 7/1997 | Gole et al. | |
| 5,729,958 A | 3/1998 | Kearney et al. | |
| 6,010,719 A * | 1/2000 | Remon et al. | 424/464 |
| 6,337,082 B1 | 1/2002 | Fuisz et al. | |
| 2002/0114833 A1* | 8/2002 | Abu-Izza et al. | 424/465 |
| 2002/0197321 A1* | 12/2002 | Seager | 424/486 |
| 2006/0073188 A1 | 4/2006 | Goutay et al. | |

FOREIGN PATENT DOCUMENTS

| | | |
|---|---|---|
| DE | 107208 | 7/1974 |
| DE | 10137232 | 2/2003 |
| EP | 0271079 | 6/1988 |
| EP | 0 278 877 A1 | 8/1988 |
| EP | 0 346 622 A2 | 12/1989 |
| EP | 0537070 | 4/1993 |
| EP | 1243256 A1 | 9/2002 |
| GB | 1548022 A | 7/1979 |
| GB | 2360210 | 9/2001 |
| GB | 2 378 383 A | 2/2003 |
| JP | 61-118314 A | 6/1966 |
| JP | 5-344619 A | 12/1993 |
| JP | 7-508676 A | 9/1995 |
| JP | 8-508247 A | 9/1996 |
| JP | 2001-521007 A | 11/2001 |
| JP | 2002-326953 A | 11/2002 |
| JP | 2003-507414 A | 2/2003 |
| WO | WO-91/09591 A1 | 7/1991 |
| WO | 9319741 | 10/1993 |
| WO | WO 94/12142 A1 | 6/1994 |
| WO | WO 94/20070 A1 | 9/1994 |
| WO | 9739698 | 10/1997 |
| WO | WO-99/21579 A1 | 5/1999 |
| WO | WO 99/21579 A1 | 5/1999 |
| WO | 9947680 | 9/1999 |
| WO | WO 00/44351 * | 8/2000 |
| WO | WO-00/44351 A1 | 8/2000 |
| WO | 0051568 | 9/2000 |
| WO | 0051593 | 9/2000 |
| WO | 00/57856 A1 | 10/2000 |
| WO | 0061117 | 10/2000 |
| WO | WO 01/13896 A1 | 3/2001 |
| WO | 0139800 | 6/2001 |
| WO | WO 01/30288 A1 | 6/2001 |
| WO | WO 01/30383 A2 | 6/2001 |
| WO | 0151082 | 7/2001 |
| WO | 0156611 | 8/2001 |
| WO | WO-02/13858 A1 | 2/2002 |
| WO | 0240676 | 5/2002 |
| WO | 03096869 | 11/2003 |

OTHER PUBLICATIONS

Hill et al., Teh ACVD task force on canine atopic dermatitis (IV): Environmental allergens, Vetrinary Immunology and Immunopathology 81 (2001) 169-186.*
Remington's Pharmaceutical Sciences, A. R. Gennaro editor, Eighteenth Edition, 1990, pp. 1305 and 1326.*
Database WPI Section Ch, Week 197437 Derwent Publications Ltd. XP002257644, Jul. 20, 1974, Abstract.
Pradalier, et al., 1999. "Sublingual-swallow immunotherapy (SLIT) with a standardized five-grass-pollen extract (drops and sublingual tablets) versus placebo in seasonal rhinitis". Allergy 54, pp. 819-828.
Chr. Hansen Group, Announcement of ALK-Abello's Pipeline, Announcement No. 14 of 27, Apr. 27, 2001.
Product Insert and Translation (2002), 8 pages.
Abecassis, et al., 1984. "Fabrication du medicament homeopathique," pp. 77-79.
Allergy Principles and Practice, 1993, vol. 1, Fourth Edition, p. 520.
Ramirez, et al., 1997. "Group 5 determination in Pooidae grass pollen extracts by monoclonal antibody-based ELISA. Correlation with biologic activity". Allergy 52, pp. 806-813.
Ipsen, et al., 1993. "Allergenic Extracts", Basic Science, Part 1, Chapter 20, pp. 540-547.

(Continued)

*Primary Examiner* — Robert A Wax
*Assistant Examiner* — Aradhana Sasan
(74) *Attorney, Agent, or Firm* — Birch, Stewart, Kolasch & Birch, LLP

(57) ABSTRACT

The present invention provides a non-compressed fast-dispersing solid dosage form suitable for oromucosal administration of a pharmaceutically active substance comprising (a) a first matrix forming agent in the form of maltodextrin having a dextrose equivalent (DE) of between 1 and 20,
(b) a second matrix forming agent in the form of sorbitol, and
(c) the active substance.

26 Claims, No Drawings

OTHER PUBLICATIONS

Haugaard, et al., 1993. "A controlled dose-response study of immunotherapy with standardized, partially purified extract of dust mite: Clinical efficacy and side effects". J. Allergy Clin. Immunol. 91, No. 3, pp. 709-722.

Elisa Competition Assay, 1993, Quantitative determination of relative potency of allergenic extracts, pp. 15-25.

European Pharmacopoeia, 1997, Third Edition, No. 2.5.12, p. 66.

European Pharmacopoeia, 1997, Third Edition, pp. 356-358.

The European Agency for the Evaluation of Medicinal Products, Human Medicines Evaluation Unit, Committee for Proprietary Medicinal Products (CPMP), London, Mar. 13, 1996, pp. 1-6.

ICH Harmonised Tropartite Guideline, Feb. 2003, "Stability Testing of New Drug Substances and Products Q1A (R2)". Internal Conference on Harmonisation of Technical Requirements for Registration of Pharmaceuticals for Human Use, pp. 1-15.

Durham, et al., "Long-Term Clinical Efficacy of Grass-Pollen Immunotherapy". The New England Journal opf Medicine, Aug. 12, 1999, pp. 468-474.

European Pharmacopoeia, Third Edition, 1997, Pharmaceutical Technical Procedures, pp. 134-135.

Lima, et al., 2002. "Grass pollen sublingual immunotherapy for seasonal rhinoconjunctivitis: a randomized controlled trial". Clin. Exp. Allergy, vol. 34, No. 2, Abstract.

CHR Hansen Group, Improving the Quality of Food and Health for People All Over the World, Annual Report, Sep. 2001, pp. 27-28.

Lowenstein, H., 1980. Arb Paul Erlich Institute 75, pp. 122-132.

Japanese Office Action dated Apr. 5, 2010 for corresponding Japanese Application No. 2006-501528.

* cited by examiner

DOSAGE FORM HAVING A SACCHARIDE MATRIX

TECHNICAL FIELD

This invention relates to a non-compressed fast dispersing solid dosage form suitable for administration of a pharmaceutically active substance and for preparing a compressed fast dispersing tablet.

BACKGROUND OF THE INVENTION

Allergy is a major health problem in countries where Western lifestyle is adapted. Furthermore, the prevalence of allergic disease is increasing in these countries. Although allergy in general may not be considered a life-threatening disease, asthma annually causes a significant number of deaths. An exceptional prevalence of about 30% in teenagers conveys a substantial loss in quality of life, working days and money, and warrants a classification among major health problems in the Western world.

Allergy is a complex disease. Many factors contribute to the sensitisation event. Among these is the susceptibility of the individual defined by an as yet insufficiently understood interplay between several genes. Another important factor is allergen exposure above certain thresholds. Several environmental factors may be important in the sensitisation process including pollution, childhood infections, parasite infections, intestinal microorganisms, etc. Once an individual is sensitised and the allergic immune response established, the presence of only minute amounts of allergen is efficiently translated into symptoms.

The natural course of allergic disease is usually accompanied by aggravation at two levels. Firstly, a progression of symptoms and disease severity, as well as disease progression, for example from hay fever to asthma. Secondly, dissemination in offending allergens most often occurs resulting in allergic multi-reactivity. Chronic inflammation leads to a general weakening of the mucosal defense mechanisms resulting in unspecific irritation and eventually destruction of the mucosal tissue. Infants may become sensitised primarily to foods, i.e. milk, resulting in eczema or gastrointestinal disorders; however, most often they outgrow these symptoms spontaneously. These infants are at risk of developing inhalation allergy later in their lives.

The most important allergen sources are found among the most prevalent particles of a certain size in the air we breathe. These sources are remarkably universal and include grass pollens and house dust mite faecal particles, which together are responsible for approximately 50% of all allergies. Of global importance are also animal dander, i.e. cat and dog dander, other pollens, such as mugwort pollens, and microfungi, such as Alternaria. On a regional basis yet other pollens may dominate, such as birch pollen in Northern and Central Europe, ragweed in the Eastern and Central United States, and Japanese cedar pollen in Japan. Insects, i.e. bee and wasp venoms, and foods each account for approximately 2% of all allergies.

Allergy, i.e. type I hyper-sensitivity, is caused by an inappropriate immunological reaction to foreign non-pathogenic substances. Important clinical manifestations of allergy include asthma, hay fever, eczema, and gastro intestinal disorders. The allergic reaction is prompt and peaks within 20 minutes upon contact with the offending allergen. Furthermore, the allergic reaction is specific in the sense that a particular individual is sensitised to particular allergen(s), whereas the individual does not necessarily show an allergic reaction to other substances known to cause allergic disease. The allergic phenotype is characterized by a pronounced inflammation of the mucosa of the target organ and by the presence of allergen specific antibody of the IgE class in the circulation and on the surface of mast-cells and basophils.

An allergic attack is initiated by the reaction of the foreign allergen with allergen specific IgE antibodies, when the antibodies are bound to high affinity IgE specific receptors on the surface of mast-cells and basophils. The mast-cells and basophils contain preformed mediators, i.e. histamine, tryptase, and other substances, which are released upon cross-linking of two or more receptor-bound IgE antibodies. IgE antibodies are cross-linked by the simultaneous binding of one allergen molecule. It therefore follows that a foreign substance having only one antibody binding epitope does not initiate an allergic reaction. The cross-linking of receptor bound IgE on the surface of mast-cells also leads to release of signaling molecules responsible for the attraction of eosinophils, allergen specific T-cells, and other types of cells to the site of the allergic response. These cells in interplay with allergen, IgE and effector cells, lead to a renewed flash of symptoms occurring 12-24 hours after allergen encounter (late phase reaction).

Allergy disease management comprises diagnosis and treatment including prophylactic treatments. Diagnosis of allergy is concerned with by the demonstration of allergen specific IgE and identification of the allergen source. In many cases a careful anamnesis may be sufficient for the diagnosis of allergy and for the identification of the offending allergen source material. Most often, however, the diagnosis is supported by objective measures, such as skin prick test, blood test, or provocation test.

The therapeutic options fall in three major categories. The first opportunity is allergen avoidance or reduction of the exposure. Whereas allergen avoidance is obvious e.g. in the case of food allergens, it may be difficult or expensive, as for house dust mite allergens, or it may be impossible, as for pollen allergens. The second and most widely used therapeutic option is the prescription of classical symptomatic drugs like anti-histamines and steroids. Symptomatic drugs are safe and efficient; however, they do not alter the natural cause of the disease, neither do they control the disease dissemination. The third therapeutic alternative is specific allergy vaccination that in most cases reduces or alleviates the allergic symptoms caused by the allergen in question.

Conventional specific allergy vaccination is a causal treatment for allergic disease. It interferes with basic immunological mechanisms resulting in persistent improvement of the patients' immune status. Thus, the protective effect of specific allergy vaccination extends beyond the treatment period in contrast to symptomatic drug treatment. Some patients receiving the treatment are cured, and in addition, most patients experience a relief in disease severity and symptoms experienced, or at least an arrest in disease aggravation. Thus, specific allergy vaccination has preventive effects reducing the risk of hay fever developing into asthma, and reducing the risk of developing new sensitivities.

The immunological mechanism underlying successful allergy vaccination is not known in detail. A specific immune response, such as the production of antibodies against a particular pathogen, is known as an adaptive immune response. This response can be distinguished from the innate immune response, which is an unspecific reaction towards pathogens. An allergy vaccine is bound to address the adaptive immune response, which includes cells and molecules with antigen specificity, such as T-cells and the antibody producing B-cells. B-cells cannot mature into antibody producing cells without help from T-cells of the corresponding specificity. T-cells that participate in the stimulation of allergic immune responses are primarily of the Th2 type. Establishment of a new balance between Th1 and Th2 cells has been proposed to be beneficial and central to the immunological mechanism of specific allergy vaccination. Whether this is brought about by a reduction in Th2 cells, a shift from Th2 to Th1 cells, or an up-regulation of Th1 cells is controversial. Recently, regulatory T-cells have been proposed to be important for the mechanism of allergy vaccination. According to this model regulatory T-cells, i.e. Th3 or Tr1 cells, down-regulate both Th1 and Th2 cells of the corresponding antigen specificity. In spite of these ambiguities it is generally believed that an active vaccine must have the capacity to stimulate allergen specific T-cells, preferably TH1 cells.

Specific allergy vaccination is, in spite of its virtues, not in widespread use, primarily for two reasons. One reason is the inconveniences associated with the traditional vaccination programme that comprises repeated vaccinations i.a. injections over a several months. The other reason is, more importantly, the risk of allergic side reactions. Ordinary vaccinations against infectious agents are efficiently performed using a single or a few high dose immunizations. This strategy, however, cannot be used for allergy vaccination since a pathological immune response is already ongoing.

Conventional specific allergy vaccination is therefore carried out using multiple subcutaneous immunizations applied over an extended time period. The course is divided in two phases, the up dosing and the maintenance phase. In the up dosing phase increasing doses are applied, typically over a 16-week period, starting with minute doses. When the recommended maintenance dose is reached, this dose is applied for the maintenance phase, typically with injections every six weeks. Following each injection the patient must remain under medical attendance for 30 minutes due to the risk of anaphylactic side reactions, which in principle although extremely rare could be life-threatening. In addition, the clinic should be equipped to support emergency treatment. There is no doubt that a vaccine based on a different route of administration would eliminate or reduce the risk for allergic side reactions inherent in the current subcutaneous based vaccine as well as would facilitate a more widespread use, possibly even enabling self vaccination at home.

Attempts to improve vaccines for specific allergy vaccination have been performed for over 30 years and include multifarious approaches. Several approaches have addressed the allergen itself through modification of the IgE reactivity. Others have addressed this route of administration.

The immune system is accessible through the oral cavity and sublingual administration of allergens is a known route of administration.

Conventionally allergy vaccine using the oromucosal route consists of the up to daily dosing of a solution of the allergen. In comparison, the therapeutic (accumulated) maintenance doses given exceeded the maintenance of the comparable subcutaneous dose by a factor 5-500. Obvious drawbacks of this dosage form and route of administration are the problems associated with accurate and uniform self administration of the correct dose by the patient (several drops may have to be given, uniformity of the individual drops, application site accuracy, etc.). There is additionally a need to refrigerate the drug and include preservatives in the formulation.

Netien et al.: "Galenica 16—Médicaments homéopathiques" ed. 2, 1986, pages 77-99 discloses a liquid solution impregnated onto a solid particulate (granules) or conventional compressed tablets of lactose, saccharose or a mixtures of these for sublingual administration of medicaments such as allergens. However these dosage forms are associated with serious drawbacks, such as the impregnation procedure.

DD-A-0 107 208 discloses a process for preparing a conventional compressed tablet containing an allergen. Upon administration the tablet is dissolved by the saliva and the allergen is then absorbed through the mucosa of the oral cavity. The formulation contains a water insoluble excipient, namely talcum as well as paraffin and fatty acids which is not desirable since it will leave an unpleasant remnant in the mouth of the patient. Moreover, the friction during the tabletting process may be detrimental to the physical stability of the allergens.

EP 278 877 discloses a pharmaceutical composition for sublingual use, where a solid support. e.g. saccharose/lactose, is coated with a solution of an allergen. The resulting formulation is alleged to disintegrate rapidly, but not instantaneously. However, there is no disclosure of how to achieve the objective. Moreover, the formulation contains reducing sugars in the form of lactose, which are prone to react with allergens.

In order to ensure that as much as possible of an administered dose of a certain allergen is presented to the mucosa of the oral cavity and additionally that the contact time of the disintegrated product with the mucosa is maximised, it is very important that the dosage form disintegrates instantaneously upon contact with the saliva of the oral cavity. Fast dispersing solid dosage forms, which readily release the active ingredient in the oral cavity are known in the art.

U.S. Pat. No. 4,371,516 discloses pharmaceutical dosage forms containing active ingredients, which disintegrate rapidly in water. The pharmaceutical dosage forms comprise an open matrix network of carrier material, which disintegrate within 10 seconds.

A freeze-dried fish gelatine based carrier as disclosed in WO 00/61117 is designed to release the active ingredient instantaneously upon contact with saliva when administered in the oral cavity. As active ingredient a vaccine against hayfever is mentioned.

A freeze-dried modified starch carrier as disclosed in WO 00/44351 is designed to release the active ingredient instantaneously upon contact with saliva when administered in the oral cavity. As active ingredient a vaccine against hayfever is mentioned. The modified starch carrier may be a dextrin and a pre-gelatinized starch.

WO 99/21579 discloses a fast-dispersing dosage form comprising a vaccine and an adjuvant for oral use.

WO 02/13858 discloses fast dissolving pharmaceutical composition containing vaccines in the form of a fast dissolving "cake" for oral use. The object of WO 02/13858 appears to be to provide viral or bacterial vaccines that will stay intact in the gastrointestinal tract. This is achieved by protecting the antigen against the acidic content of the stomach by incorporating antacids such as calcium carbonate into the cake.

WO 00/51568 discloses a fast-disintegrating compressed low friability tablet that is designed to dissolve in the mouth in contact with saliva in less than 30 seconds forming an easy-to-swallow suspension.

U.S. Pat. No. 5,648,093 discloses a fast dispersing non-compressed solid dosage form. In a specific example, a dosage form composed of maltodextrin, mannitol and xanthan gum is disclosed.

WO 91/09591 (Example 25) describes the preparation of a placebo carrier matrix by solid-state dissolution, wherein the matrix is composed of maltodextrin (DE10), mannitol and xanthan gum.

U.S. Pat. No. 6,337,082 describes a saccharide-based matrix for use in food products comprising maltodextrin having a DE of less than 40, preferably between 20 and 40 and alternatively between 10 and 20, a gelling agent and a sugar. The gelling agent may e.g. be xanthan gum or gelatine. Sorbitol is mentioned in a long list of suitable sugars. The matrix is stated to be instantaneously dispersible in water to form a suspension. The matrix is formed in a process involving simultaneous flash heating and applied physical force. The resulting matrix has the form of particles, chips, flakes or spicules. The Examples mention a specific composition of maltodextrin having a DE of 36, sorbitol and a food ingredient, which is spun to form a matrix of a white, narrow flake.

WO 00/57856 discloses a fast-dispersing dosage form pharmaceutical for administration upon contact with the buccal membrane, the dosage form comprising between 50% and 99% of a carrier and possibly a diluent. As carrier maltodextrin having a DE of between 3 and 50 is mentioned from a long list of compounds. Sorbitol is mentioned as diluent from a long list of compounds.

SUMMARY OF THE INVENTION

The present invention relates, inter alia, to the following:

A non-compressed fast-dispersing solid dosage form suitable for oromucosal administration of a pharmaceutically active substance comprising
(a) a first matrix forming agent in the form of maltodextrin having a dextrose equivalent (DE) of between 1 and 20,
(b) a second matrix forming agent in the form of sorbitol, and
(c) the active substance.

A dosage form according to the invention comprising one or more further matrix forming agents.

A dosage form according to the invention, wherein the further matrix forming agent is a mono-, di- or tri-saccharide.

A dosage form according to the invention, wherein the further matrix forming agent is mannitol.

A dosage form according to the invention further comprising polyethylene glycol (PEG).

A dosage form according to the invention, wherein maltodextrin is present in an amount of 3-40% (w/w), preferably 10-35 (w/w) and more preferably 15-25% (w/w) of the dosing solution.

A dosage form according to the invention, wherein mannitol is present in an amount of 1-20% (w/w), preferably 2-10% (w/w) and more preferably 3-6 (w/w) of the dosing solution.

A dosage form according to the invention, wherein sorbitol is present in an amount of 0.01-10% (w/w), preferably 0.05-5% (w/w) and more preferably 0.1-2% (w/w) of the dosing solution.

A dosage form according to the invention, wherein PEG is present in an amount of 1-20% (w/w), preferably 2-15% (w/w) and more preferably 3-10% (w/w) of the dosing solution.

A dosage form according to the invention, wherein the active substance is an allergen.

The present invention is based on the surprising finding that it is possible to use maltodextrin as primary matrix forming agent in a fast-dispersing non-compressed dosage form instead of conventional primary matrix forming agents, such as gelatine and starch. Maltodextrin has the advantage over starch that it dissolves or disperses more quickly, as maltodextrin is partly hydrolysed. At the same time, it has surprisingly been found that non-compressed solid dosage forms using maltodextrin as matrix forming agent has sufficient mechanical strength to remain stable and intact during manufacture, packaging, transport, handling and storage so as to avoid degradation of active substance and release of active substance from the dosage form, which is highly undesirable for some active substances, such as allergens.

Furthermore, it has surprisingly been shown that sorbitol, even in very small contents, strongly increases the mechanical strength of the dosage form.

DETAILED DESCRIPTION OF THE INVENTION

A non-compressed fast dispersing solid dosage form, which is designed to release the active ingredient almost instantaneously in the oral cavity on contact with saliva is very suitable for the delivery of the allergens to the mucosa oromucosally. However, a priori the use of this particular dosage form for allergens is associated with severe problems. This type of solid dosage form is namely characterized by a low mechanical strength compared to compressed tablets due to the inherent nature of the non-compressed matrix, which is almost wafer-like and fragile. This may result in the release of residual particles containing the allergen during handling of the dosage form by the patient. This is especially detrimental when the active ingredient is an allergen, because the allergen can elicit an allergic reaction in a disposed person or induce an allergic reaction, that sensitisation or allergic response being dose dependent. Maximum allowable levels for environmental contamination in the form of e.g. allergen in dust have been proposed depending on the allergen in question as low as 2 micro gram major allergen per gram house dust. (Allergy. Principles and practice (1993, 4. ed.), Mosby-Year book, Vol. I page 520).

Such non-compressed fast dispersing solid dosage forms, which are manufactured by removal of a liquid from a solidified system comprising matrix forming agents, active ingredient and other suitable excipients may be manufactured in situ.

Due to the in situ manufacturing process, i.e. removal of the solvent from a solidified system of the active ingredient and the matrix forming excipients in the final container, i.e. blister packs, it is not possible to coat the dosage form in order to seal it and thus preventing the release of residues from the dosage form. Moreover, coating the dosage form is not possible, because it would jeopardize the instantaneous release properties of the dosage form.

Thus, there exists a need for a fast dispersing solid dosage form containing allergens, which quickly releases the allergen in the oral cavity, and where the dosage form at the same time has such a mechanical robustness, so ideally no residues will be released from the dosage form to the environment during handling of the dosage form by the patient.

Further, there is the need for a fast dispersing solid dosage forms containing allergens to have sufficient chemical stability of the active ingredients to allow the manufacture, transportation, storage and especially patient handling.

It has now surprisingly been found that it is indeed possible to manufacture a low friable non-compressed fast dispersing solid dosage form containing allergens, which is sufficiently robust and does not release hazardous amounts of residue upon handling by the patient. Moreover, it has surprisingly been found that these formulations are indeed stable at room temperature. This finding has significant importance for the handling procedures of the final product. Cold storage at the manufacturing plant, during transport or during storage at the pharmacy is often associated with high cost, since the cooling facilities have to be closely monitored and it is also very expensive to invest in reliable cooling facilities. Moreover, with respect to compliance of the patient, it is also preferable that the dosage form can be stored at room temperature. The European Pharmacopeia monograph for Allergen Products states that the moisture levels should not exceed 5% for freeze-dried products (i.e. allergen extracts in vials). It has surprisingly been found that even the dosage forms according to the invention having water content above the required maximum level of 5% are stable at room temperature. Without being bound to theory it may be explained by the fact that the excipients of the fast dispersing solid dosage form binds the remaining water in the dosage form and reduces the water activity of the allergen vaccine dosage formulation. Hence, by reducing the water activity of the formulation, it is possible to obtain a stable formulation with no degradation of the allergen, even though the water content is higher than maximum level of 5%, which is prescribed for allergen extracts in vials.

Stability of the solid dosage form in order to ensure a sufficient shelf life of the final product may be measured with reference to physical and chemical properties of the solid dosage form or its individual constituents.

Water activity is one important factor contributing to the shelf life of a product. It is well known that the water activity of a product affects growths of bacteria as well as the stability, the potency and consistency of pharmaceuticals. Also protein stability is influenced significantly by water activity due to their relatively fragile nature. Most proteins must maintain conformation to remain active. Maintaining low water activity levels helps to prevent or entice conformational changes, which subsequently is important to ensure that a protein in the form of an allergen is stable. Also hydrolytic degradation of proteins whether caused by enzymes or not is affected by the water activity.

Water activity measurements are carried out by using methods known to the person skilled in the art for example chilled mirror dew point technology, relative humidity with sensors that change electrical resistance or capacitance or using a lithium chloride electrode.

The water activity of a solid dosage form preferable does not exceed 25% and preferably be between 0.1%-20%, more preferably between 0.5-15%, more preferably 2-8%, most preferably between 4-7%.

The water content of a solid dosage form determined according to the method described in example 1 does preferably not exceed 25% and preferably be between 0.1%-20%, more preferably between 0.5-15%, more preferably 2-8%, most preferably between 4-7%.

Several laboratory tests are available for characterising an allergen. The most widely used techniques are sodium dodecyl sulphate polyacrylamide gel electrophoresis (SDS-PAGE), isoelectric focusing (IEF), crossed immunoelectrophoresis (CIE) and Rocket Immuno Electrophoresis (RIE). The quantification of individual allergens may be performed by a variety of quantitative immunoelectrophoretic techniques (QIE), Radial Immune Diffusion (RIE) or by enzyme-linked immunosorbent assays (ELISA). The determination of total allergenic potency is most frequently performed by radio allergosorbent test (RAST), (LIA) or related techniques. ELISA-based techniques may also be used.

Guidance to the normally applied acceptable limit for test measuring biopotency are found e.g. in Note for Guidance on Allergen Product; The European Agency for the Evaluation of Medicinal Product, CPMP_BWP_243_96.

Preferably for the purpose of this invention the stability of the active ingredient i.a. the allergen is assessed by means of potency measurements of the allergen like total allergen activity and major allergen content.

The "initial allergenic activity" or the "initial content of at least one major allergens" of a solid dosage form means the value as after the completion of the manufacturing of the solid dosage form.

Loss in total allergen activity according the method described in example 1 should preferably be less than 50% of the total initial activity, more preferably less than 30% of the total initial activity, even more preferably be less than 20% of the total initial activity, most preferably less than 15% of the total initial activity.

The classification of an allergen as a major allergen can be subject to several tests. Allergens are commonly classified as major allergen if at least 25% of the patients shows strong IgE binding (score 3) and at least moderate binding (score 2) from 50% of the patients, the binding being determined by an CRIE (CRIE Strong binding i.e. visible IgE-binding on a x-ray film after one day, CRIB Moderate binding i.e. binding after 3 days, CRIE Weak binding i.e. binding after 10 days). Strong IgE binding from at least 10% of the patients classifies the allergen as an Intermediate allergen and clearly specific binding from less than 10% of the patients gives a Minor allergen. Other methods may also be used in determining the IgE binding of for instance IgE-blots.

Loss in the allergen content of at least one major allergen according to the method described in example 1 is preferably less than 50% of the total initial content, more preferably less than 30% of the total initial content, even more preferably less than 20% of the total initial content, most preferably less than 15% of the initial content.

In one embodiment of the solid allergen dosage form the loss in total allergen activity according the method described in example 1 is less than 50% of the total initial activity.

In another embodiment of the solid allergen dosage the loss allergen content of at least one major allergen according to the method described in example 1 is less than 50% of the initial content.

The dosage form of the invention is preferably stable in the sense that it does not significantly change after manufacture with respect to physical and chemical properties e.g. potency of the allergen, mechanical robustness and organoleptical properties in order to ensure a sufficient shelf life of the final product.

Thus, the stability of the solid dosage form is preferably assessed by additional parameters, such as mechanical robustness like friability, tensile strength, peak load to fracture, stability of physical properties, inter alia, the dispersion time and stability of organoleptical properties like visual appearance of the dosage form.

These can be evaluated by e.g. measurements of Peak load to fracture or tensile strength of the solid dosage forms of the current invention. As it is apparent from the equation from which the tensile strength can be calculated, the tensile strength value obtained depend of a number of parameter, which are subject to variation e.g. thickness or diameter of the solid dosage form and will contribute to the variation of value. Therefore Peak load to fracture is believed to be a even more accurate parameter for evaluation of the robustness of the solid dosage units of the current invention In order to ensure that the solid dosage form is sufficient robust during storage and when handled by the patient, the dosage form needs to have a certain resistance to external force, but at the same time ensure that the solid dosage form disintegrates quickly in the mouth.

In a further embodiment of the current invention the solid dosage form preferably has a tensile strength less than 1.1 N/mm2, more preferably less than 0.8 N/mm2. Typically, the dosage form has a tensile strength of between 0.2 and 0.5

N/mm2. The lower the tensile strength is, the lower the mechanical strength and stability of the dosage form, and the faster it disperses.

Preferably fast dispersing dosage form disintegrates instantaneously or quickly in the mouth upon contact with the saliva in order to ensure maximum exposure of allergen to immune competent tissue of the mucosa before swallowing. In a preferred embodiment the solid dosage form disintegrates in less than about 90 seconds, preferably in less than 60 seconds, preferably in less than 30 seconds, more preferably in less than 20, more preferably in 15 seconds, even more preferably in less than 10 seconds in the oral cavity, even more preferably in less than 5, most preferably in less than about 2 sec.

In a preferred embodiment of the invention, the compositions of the invention are fast dispersing solid dosage forms comprising a solid network of the allergen and any water-soluble or water-dispersible matrix. The network is obtained by subliming solvent from a composition in the solid state, the composition comprising a solution of the allergen and the matrix. More preferably the network is obtained by lyophilization.

Excipients

In a preferred embodiment of the invention, the dosage form further comprising one or more excipients in addition the matrix forming agent.

Pharmaceutically acceptable excipients forming part of the matrix in the fast dispersing solid dosage form according to invention are suitable excipients such as adjuvants, antacids, diluents, enhancers, mucoadhesive agents, flavouring agents, taste masking agents, preservatives, antioxidants, surfactants, viscosity enhancers, colouring agents, pH modifiers, sweeteners etc. These excipients are all selected in accordance with conventional pharmaceutical practice in a manner understood by the persons skilled in the art of formulating allergen vaccines.

In a preferred embodiment of the invention, the dosage form contains a protein stabilizing agent. Examples of protein stabilising agents are polyethylene glycols (PEG), e.g. PEG300, PEG400, PEG600, PEG1000, PEG1500, PEG3000, PEG3050, PEG4000, PEH6000, PEG20000 and PEG35000; amino acids, such as glycin, alanine, arginine; mono-, di and tri-saccharides, such as trehalose and sucrose; polyvinylalcohol (PVA); polyoxyethylene sorbitan fatty acid esters (polysorbates, tweens or span); human serum albumin (HSA); bovine serum albumin (BSA). Preferably, PEG is used as protein stabilising agent. In addition to being a protein stabiliser, PEG is believed to confer the property of elasticity to the matrix of the dosage form.

Suitable colouring agents include red, black and yellow iron oxides and FD & C dyes such as FD & C blue No. 2 and FD & C red No. 40. Suitable flavouring agents include mint, raspberry, liquorice, orange, lemon, grapefruit, caramel, vanilla, cherry and grape flavours and combination of these. Suitable pH modifiers include citric acid, tartaric acid, phosphoric acid, hydrochloric acid and maleic acid. Suitable sweeteners include aspartame, acesulfame K and thaumatin. Suitable taste-masking agents include sodium bicarbonate, ion-exchange resins, cyclodextrin inclusion compounds, adsorbates or microencapsulated actives.

Adjuvants are normally used to enhance the absorption of the allergen as well as to enhance the immune-stimulating properties of the allergen.

In one embodiment of the invention at least one adjuvant is incorporated into the dosage form according to the invention. Examples of suitable adjuvants are aluminium salts, non-toxic bacterial fragments, cytokines, chlorea toxin (and detoxified fractions thereof), chitosan, homologous heat-labile of *E.coli* (and detoxified fractions thereof), saponins, bacterial products such as lipopoly-saccharides (LPS) and muramyl dipeptide (MDP), liposomes, CpG (immunostimulatory DNA sequences), lactide/glycolide homo (copolymers in the form of microparticular polymers etc. The use of adjuvants in allergen vaccines are often reasoned by the fact the allergens in question are not able to penetrate the barrier to be passed. The adjuvants thus may serve as absorption enhancing agents or they may act as immunostimulants. The use of adjuvants may, however, be associated with serious draw backs such as unintended stimulation of various mechanisms of the immune response, systemic lupus erythematosus or affecting the barrier capabilities of the mucosal membranes and thus allowing the passage of hazardous substances. Further from an industrial point of view addition of an adjuvant further constitute further manufacturing and material cost besides the large demand for documentation in respect to drug registration.

In another preferred embodiment of the invention the fast dispersing solid dosage form according to the invention does not comprise an adjuvant.

It has also surprisingly been found that it is not necessary to incorporate an adjuvant into the fast dispersing solid dosage form in order to enhance the immune-stimulating properties of the allergen in question i.e. that the solid dosage form is capable of raising a specific immune response.

The non-compressed fast dispersing solid dosage form according to the invention may be mucoadhesive to some extent in itself, however in a preferred embodiment of the invention, it may be necessary to further add mucoadhesive excipients to said dosage form in order to increase the contact time of the dosage form with the mucosa of the oral cavity. Suitable mucoadhesive excipients are polyacrylic polymers such as carbomer and carbomer derivatives; cellulose derivatives such as hydroxypropylmethylcellulose, hydroxyethylcellulose, hydroxypropylcellulose and sodium carboxymethylcellulose; natural polymers such as gelatine, sodium alginate, pectin and glycerol.

Matrix Forming Agent

In a preferred embodiment of the invention, maltodextrin has a DE of between 1 and 15, more preferably between 1 and 10.

In a preferred embodiment of the invention the further matrix forming agent is a mono-, di- or tri-saccharide. Examples of mono-, di- and tri-saccharides are mannose, glucose, galactose, mannitol, mannose, galactitol, erythritol, inositol, threitol, maltitol, trehalose, sucrose, maltose, maltotriose, lactose, palatinose and lactulose. Preferred mono-, di- and tri-saccharide are mannose and mannitol.

In a preferred embodiment of the dosage form of the invention, the further matrix forming agent is mannitol.

Other matrix forming agents suitable for use according to the present invention include substances derived from animal or vegetable proteins, such as gelatines, soy, wheat and psyllium seed proteins; gums, such as acacia, guar, agar and xanthan; polysaccharides, such as starch and modified starch; cyclic sugars such as cyclodextrin; alginates; carboxymethylcellulose; carrageenans; dextrans; pectins; synthetic polymers, such as polyvinylpyrrolidone; and polypeptide/protein or polysaccharide complexes such as gelatine-acacia complexes.

Other matrix forming agents suitable for use according to the present invention inorganic salts such as sodium phosphate, sodium chloride and aluminium silicates; and amino acids having from 2 to 12 carbon atoms such as a glycine, L-alanine, L-aspartic acid, L-glutamic acid, L-hydroxyproline, L-isoleucine, L-leucine and L-phenylalanine.

As mentioned above the present invention has provided a possibility of producing fast dispersing non-compressed dosage forms using maltodextrin as primary matrix forming agent and sorbitol as secondary matrix forming agent.

Furthermore, the present invention has provided a possibility of producing fast dispersing non-compressed dosage forms with a matrix composed of maltodextrin, sorbitol and mono-, di- and trisaccharides. Thus, in another preferred embodiment of the invention, the matrix is free of other matrix forming agents than maltodextrin, sorbitol and mono-, di- and trisaccharides. In particular, the matrix is preferably free of polymeric matrix forming agents, and more specifically the matrix is preferably free of gelatines and/or starch and/or gums.

The total dry matter content of the dosing solution is preferably above 20% (w/w), more preferably above 30% (w/w), more preferably above 40% (w/w), more preferably above 50% (w/w) and most preferably above 60% (w/w). The total dry matter content of the dosing solution will depend on the dimensions of the tablet to be produced.

Pharmaceutically Active Substance

The pharmaceutically active substance used in the dosage form of the invention may be any active substance, which is capable of being administered through the oromucosal route. Oromucosal administration is particularly relevant, when a quick administration is desired and/or where administration via the intestinal mucosa is difficult, e.g. because of difficulties in the transport of the active substance across the mucosa and/or because of degradation of the active substance through the passage of the gastro-intestinal system. Administration via the oromucosal route is e.g. relevant for proteins.

Examples of suitable active substances include, but are not limited to:

Analgesics and anti-inflammatory agents: aloxiprin, auranofm, azapropazone, benorylate, diflunisal, etodolac, fenbufen, fenoprofen calcium, flurbiprofen, ibuprofen, indomethacin, ketoprofen, meclofenamic acid, mefenamic acid, nabumetone, naproxen, oxaprozin, oxyphenbutazone, phenylbutazone, piroxicam, sulindac.

Anthelmintics: albendazole, bephenium hydroxynaphthoate, cambendazole, dichlorophen, ivermectin, mebendazole, oxamniquine, oxfendazole, oxantel embonate, praziquantel, pyrantel embonate, thiabendazole.

Anti-arrhythmic agents: amiodarone HCl, disopyramide, flecainide acetate, quinidine sulphate.

Anti-bacterial agents: benethamine penicillin, cinoxacin, ciprofloxacin HCl, clarithromycin, clofazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphamerazine, sulphacetamide, sulphadiazine, sulphafurazole, sulphamethoxazole, sulphapyridine, tetracycline, trimethoprim.

Anti-coagulants: dicoumarol, dipyridamole, nicoumalone, phenindione.

Anti-depressants: amoxapine, ciclazindol, maprotiline HCl, mianserin HCl, nortriptyline HCl, trazodone HCl, trimipramine maleate.

Anti-diabetics: acetohexamide, chlorpropamide, glibenclamide, gliclazide, glipizide, tolazamide, tolbutamide.

Anti-epileptics: beclamide, carbamazepine, clonazepam, ethotoin, methoin, methsuximide, methylphenobarbitone, oxcarbazepine, paramethadione, phenacemide, phenobarbitone, phenytoin, phensuximide, primidone, sulthiame, valproic acid.

Anti-fungal agents: amphotericin, butoconazole nitrate, clotrimazole, econazole nitrate, fluconazole, flucytosine, griseofulvin, itraconazole, ketoconazole, miconazole, natamycin, nystatin, sulconazole nitrate, terbinafine HCl, terconazole, tioconazole, undecenoic acid.

Anti-gout agents: allopurinol, probenecid, sulphinpyrazone.

Anti-hypertensive agents: amlodipine, benidipine, darodipine, dilitazem HCl, diazoxide, felodipine, guanabenz acetate, indoramin, isradipine, minoxidil, nicardipine HCl, nifedipine, nimodipine, phenoxybenzamine HCl, prazosin HCL, reserpine, terazosin HCl.

Anti-malarials: amodiaquine, chloroquine, chlorproguanil HCl, halofantrine HCl, mefloquine HCl, proguanil HCl, pyrimethamine, quinine sulphate.

Anti-migraine agents: dihydroergotamine mesylate, ergotamine tartrate, methysergide maleate, pizotifen maleate, sumatriptan succinate.

Anti-muscarinic agents: atropine, benzhexol HCl, biperiden, ethopropazine HCl, hyoscine butyl bromide, hyoscyamine, mepenzolate bromide, orphenadrine, oxyphencyl-cimine HCl, tropicamide.

Anti-neoplastic agents and Immunosuppressants: aminoglutethimide, amsacrine, azathioprine, busulphan, chlorambucil, cyclosporin, dacarbazine, estramustine, etoposide, lomustine, melphalan, mercaptopurine, methotrexate, mitomycin, mitotane, mitozantrone, procarbazine HCl, tamoxifen citrate, testolactone.

Anti-protazoal agents: benznidazole, clioquinol, decoquinate, diiodohydroxyquinoline, diloxanide furoate, dinitolmide, furzolidone, metronidazole, nimorazole, nitrofurazone, ornidazole, tinidazole.

Anti-thyroid agents: carbimazole, propylthiouracil.

Anxiolytic, sedatives, hypnotics and neuroleptics: alprazolam, amylobarbitone, barbitone, bentazepam, bromazepam, bromperidol, brotizolam, butobarbitone, carbromal, chlordiazepoxide, chlormethiazole, chlorpromazine, clobazam, clotiazepam, clozapine, diazepam, droperidol, ethinamate, flunanisone, flunitrazepam, fluopromazine, flupenthixol decanoate, fluphenazine decanoate, flurazepam, haloperidol, lorazepam, lormetazepam, medazepam, meprobamate, methaqualone, midazolam, nitrazepam, oxazepam, pentobarbitone, perphenazine pimozide, prochlorperazine, sulpiride, temazepam, thioridazine, triazolam, zopiclone.

β-blockers: acebutolol, alprenolol, atenolol, labetalol, metoprolol, nadolol, oxprenolol, pindolol, propranolol.

Cardiac Inotropic agents: amrinone, digitoxin, digoxin, enoximone, lanatoside C, medigoxin.

Corticosteroids: beclomethasone, betamethasone, budesonide, cortisone acetate, desoxymethasone, dexamethasone, fludrocortisone acetate, flunisolide, flucortolone, fluticasone propionate, hydrocortisone, methylprednisolone, prednisolone, prednisone, triamcinolone.

Diuretics: acetazolamide, amiloride, bendrofluazide, bumetanide, chlorothiazide, chlorthalidone, ethacrynic acid, frusemide, metolazone, spironolactone, triamterene.

Enzymes:

Anti-parkinsonian agents: bromocriptine mesylate, lysuride maleate.

Gastro-intestinal agents: bisacodyl, cimetidine, cisapride, diphenoxylate HCl, domperidone, famotidine, loperamide, mesalazine, nizatidine, omeprazole, ondansetron HCL, ranitidine HCl, sulphasalazine.

Histamine H,-Receptor Antagonists: acrivastine, astemizole, cinnarizine, cyclizine, cyproheptadine HCI, dimenhydrinate, flunarizine HCl, meclozine HCl, oxatomide, terfenadine, triprolidine.

Lipid regulating agents: bezafibrate, clofibrate, fenofibrate, gemfibrozil, probucol.

Local Anaesthetics:

Neuro-muscular agents: pyridostigmine.

Nitrates and other anti-anginal agents: amyl nitrate, glyceryl trinitrate, isosorbide dinitrate, isosorbide mononitrate, pentaerythritol tetranitrate.

Nutritional agents: betacarotene, vitamin A, vitamin B2, vitamin D, vitamin E, vitamin K.

Opioid analgesics: codeine, dextropropyoxyphene, diamorphine, dihydrocodeine, meptazinol, methadone, morphine, nalbuphine, pentazocine.

Oral vaccines: Vaccines designed to prevent or reduce the symptoms of diseases of which the following is a representative but not exclusive list: Influenza, Tuberculosis, Meningitis, Hepatitis, Whooping Cough, Polio, Tetanus, Diphtheria, Malaria, Cholera, Herpes, Typhoid, HIV, AIDS, Measles, Lyme disease, Travellers'Diarrhea, Hepatitis A, B and C, Otitis Media, Dengue Fever, Rabies, Parainfluenza, Rubella, Yellow Fever, Dysentery, Legionnaires Disease, Toxoplasmosis, Q-Fever, Haemorrhegic Fever, Argentina Haemorrhagic Fever, Caries, Chagas Disease, Urinary Tract Infection caused by *E. coli*, Pneumoccoccal Disease, Mumps, and Chikungunya.

Vaccines to prevent or reduce the symptoms of other disease syndromes of which the following is a representative but not exclusive list of causative organisms:

*Vibrio* species, *Salmonella* species, *Bordetella* species, *Haemophilus* species, Toxoplasmosis gondii, Cytomegalovirus, *Chlamydia* species, *Streptococcal* species, Norwalk Virus, *Escherischia coli, Helicobacter pylori*, Rotavirus, *Neisseria gonorrhae, Neisseria meningiditis*, Adenovirus, Epstein Barr Virus, Japanese Encephalitis Virus, *Pneumocystis carini*, Herpes simplex, *Clostridia* species, Respiratory Syncytial Virus, *Klebsielia* species, *Shigella* species, *Pseudomonas aeruginosa*, Parvovirus, *Campylobacter* species, *Rickettsia* species, *Varicella zoster, Yersinia* species, Ross River Virus, J. C. Virus, *Rhodococcus equi, Moraxella catarrhalis, Borrelia burgdorferi* and *Pasteurella haemolytica*.

Vaccines directed to non-infections immuno-modulated disease conditions such as topical and systematic allergic conditions such as Hayfever, Asthma, Rheumatoid Arthritis and Carcinomas.

Vaccines for veterinary use include those directed to Coccidiosis, Newcastle Disease, Enzootic pneumonia, Feline leukaemia, Atrophic rhinitis, Erysipelas, Foot and Mouth disease, Swine, pneumonia, and other disease conditions and other infections and auto-immune disease conditions affecting companion and farm animals.

Proteins, peptides and recombinant drugs: insulin (hexameric/dimeric/-monomeric forms), glucagon, growth hormone (somatotropin), polypeptides or their derivatives, (preferably with a molecular weight from 1000 to 300,000), calcitonins and synthetic modifications thereof, enkephalins, interferons (especially Alpha-2 interferon for treatment of common colds), LHRH and analogues (nafarelin, buserelin, zolidex), GHRH (growth hormone releasing hormone), secretin, bradykin antagonists, GRF (growth releasing factor), THF, TRH (thyrotropin releasing hormone), ACTH analogues, IGF (insulin like growth factors), CGRP (calcitonin gene related peptide), atrial natriurectic peptide, vasopressin and analogues (DDAVP, lypressin), factor VIII, G-CSF (granulocyte-colony stimulating factor), EPO (erythropoitin).

Sex hormones: clomiphene citrate, danazol, ethinyloestradiol, medroxyprogesterone acetate, mestranol, methyltestosterone, norethisterone, norgestrel, oestradiol, conjugated oestrogens, progesterone, stanozolol, stiboestrol, testosterone, tibolone.

Spermicides: nonoxynol 9.

Stimulants: amphetamine, dexamphetamine, dexfenfluramine, fenfluramine, mazindol, pemoline.

In a preferred embodiment of the invention the pharmaceutically active substance is an allergen. In the rest of this section and in most other parts of the description the invention is described with respect to this embodiment of the invention.

According to the invention an allergen vaccine is provided in a fast dispersing solid dosage form, which rapidly dissolves in the oral cavity on contact with saliva, hence bringing the allergen in close contact with the immunological relevant tissue of the mucosa and allowing the allergen to address these. In a preferred embodiment of the invention the allergen according to the present invention is any naturally occurring protein that has been reported to induce allergic, i.e. IgE mediated reactions upon their repeated exposure to an individual. Examples of naturally occurring allergens include pollen allergens (tree-, herb, weed-, and grass pollen allergens), insect allergens (inhalant, saliva and venom allergens, e.g. mite allergens, cockroach and midges allergens, hymenopthera venom allergens), animal hair and dandruff allergens (from e.g. dog, cat, horse, rat, mouse etc.), and food allergens. Important pollen allergens from trees, grasses and herbs are such originating. from the taxonomic orders of Fagales, Oleales, Pinales and platanaceae including i.a. birch (Betula), alder (Alnus), hazel (Corylus), hornbeam (Carpinus) and olive (Olea), cedar (Cryptomeria and Juniperus), Plane tree (Platanus), the order of Poales including i.a. grasses of the genera Lolium, Phleum, Poa, Cynodon, Dactylis, Holcus, Phalaris, Secale, and Sorghum, the orders of Asterales and Urticales including i.a. herbs of the genera Ambrosia, Artemisia, and Parietaria. Other important inhalation allergens are those from house dust mites of the genus Dermatophagoides and Euroglyphus, storage mite e.g Lepidoglyphys, Glycyphagus and Tyrophagus, those from cockroaches, midges and fleas e.g. Blatella, Periplaneta, Chironomus and Ctenocepphalides, and those from mammals such as cat, dog and horse, venom allergens including such originating from stinging or biting insects such as those from the taxonomic order of Hymenoptera including bees (superfamily Apidae), wasps (superfamily Vespidea), and ants (superfamily Formicoidae). Important inhalation allergens from fungi are i.a. such originating from the genera Alternaria and Cladosporium.

In a more preferred embodiment of the invention the allergen is Bet v 1, Aln g 1, Cor a 1 and Car b 1, Que a 1, Cry j 1, Cry j 2, Cup a 1, Cup s 1, Jun a 1, Jun a 2, jun a 3, Ole e 1, Lig v 1, Pla l 1, Pla a 2, Amb a 1, Amb a 2, Amb t 5, Art v 1, Art v 2 Par j 1, Par j 2, Par j 3, Sal k 1, Ave e 1, Cyn d 1, Cyn d 7, Dac, g 1, Fes p 1, Hol l 1, Lol p 1 and 5, Pha a 1, Pas n 1, Phl p 1, Phl p 5, Phl p 6, Poa p 1, Poa p 5, Sec c 1, Sec c 5, Sor h 1, Derf 1, Der f 2, Der p 1, Der p 2, Der p 7, Der m 1, Eur m 2, Gly d 1, Lep d 2, Blo t 1, Tyr p 2, Bla g 1, Bla g 2, Per a 1, Fel d 1, Can f 1, Can f 2, Bos d 2, Equ c 1, Equ c 2, Equ c 3, Mus m 1, Rat n 1, Apis m 1, Api m 2, Ves v 1, Ves v 2, Ves v 5, Dol m 1, Dil m 2, Dol m 5, Pol a 1, Pol a 2, Pol a5, Sol i 1, Sol i 2, Sol i 3 and Sol i 4, Alt a 1, Cla h 1, Asp f 1, Bos d 4, Mald 1, Gly m 1, Gly m 2, Gly m 3, Ara h 1, Ara h 2, Ara h 3, Ara h 4, Ara h 5 or shufflant hybrids from Molecular Breeding of any of these.

In the most preferred embodiment of the invention the allergen is grass pollen allergen or a dust mite allergen or a ragweed allergen or a cedar pollen or a cat allergen or birch allergen.

In yet another embodiment of the invention the fast dispersing solid dosage form comprises at least two different types of allergens either originating from the same allergic source or originating from different allergenic sources e.g. grass group 1 and grass group 5 allergens or mite group 1 and group 2 allergens from different mite and grass species respectively, weed antigens like short and giant ragweed allergens, different fungis allergens like alternaria and cladosporium, tree allergens like birch, hazel, hornbeam, oak and alder allergens, food allergens like peanut, soybean and milk allergens.

The allergen incorporated into the fast dispersing solid dosage form may be in the form of an extract, a purified allergen, a modified allergen, a recombinant allergen or a mutant of a recombinant allergen. An allergenic extract may naturally contain one or more isoforms of the same allergen, whereas a recombinant allergen typically only represents one isoform of an allergen. In a preferred embodiment the allergen is in the form of an extract. In another preferred embodiment the allergen is a recombinant allergen. In a further preferred embodiment the allergen is a naturally occurring low IgE-binding mutant or a recombinant low IgE-binding mutant.

Allergens may be present in equi-molar amounts or the ratio of the allergens present may vary preferably up to 1:20.

In a further embodiment of the invention the low IgE binding allergen is an allergen according to WO 99/47680, WO 02/40676 or WO 03/096869 A2.

Dosage Form

The dosage form of the invention is preferably produced by lyophilisation.

Preferably pH is adjusted prior to solidification of the allergen and matrix containing solution to avoid denaturation of the allergen, precipitation and assure a stable product. The optimum pH for different allergens in solution span almost the entire pH range as does their isoelectric point (pI). Mixtures of allergens like extracts equally have optimum for solubility and stability determined by factors like the concentration of the individual allergens in the extract. Therefore an individual determination of a feasible range of pH for a formulation according to this invention may be envisaged. The optimum pH for the allergen in question is determined by carrying out accelerated stability studies with formulations with different pH. The design of such studies is known to the person skilled in the art of formulating allergen vaccines.

Preferably, dosing solutions containing an allergen extract should be adjusted to pH between 3.5-10, more preferably 4-9, most preferably 6-9.

Furthermore, it is well known in the art that ionic strength may be a parameter affecting the stability of a freeze-dried solid dosage form primarily through its effect of the freeze-drying processes. Also it is known to affect precipitation at high ionic strengths. Accordingly an optimum must be established by measurements well known to the person skilled in the art. Preferably the ionic strength of an extract of 10 μg/ml is in between 1-1500 μS/cm, more preferably between 300-800 μS/cm, most preferably about 500 μS/cm, for a matrix and allergen containing system it is preferred that the ionic strength is between 1-2000 μS/cm, more preferably 500-1500 μS/cm.

Classical incremental dosage desensitisation, where the dose of allergen in the form of a fast dispersing solid dosage form is increased to a certain maximum relieves the symptoms of allergy. The preferred potency of a unit dose of the dosage form is from 150-1000000 SQ-u/dosage form, more preferred the potency is from 500-500000 SQ-u/dosage form and more preferably the potency is from 1000-250000 SQ-u/dosage form, even more preferred 1500-125000 SQ-u/dosage form most preferable 1500-75000 SQ-u/dosage form.

In another embodiment of the invention the dosage form is a repeated mono-dose, preferably within the range of 1500-75000 SQ-u/dosage form.

In further embodiment of the invention the allergen dosage form dissolved in saliva is not swallowed until 3 min after administration in order to allow sufficient contact time for e.g. absorption over the mucosal membrane in the mouth.

In yet a further preferred embodiment the allergen dosage form is not diluted in the oral cavity e.g. by intake of a fluid like water until after 5 min.

The fast dispersing solid dosage form according to the invention may be manufactured and packaged in disposable single dose blister packs as described in U.S. Pat. No. 5,729,958 and U.S. Pat. No. 5,343,762. Examples of suitable blister packs are All Aluminium Blister packs, blister packs made of polymers e.g. polypropylene, blister packs of PVC and blister packs formed from PVC/PVdC laminate and sealed with e.g. aluminium laminated to calendered kraft paper, Aclar® or Triplex®.

In one embodiment of the invention, the fast dispersing dosage form is manufactured and packed in blister packs formed from PVC/PVdC laminate and sealed with aluminium laminated to calendered kraft paper. In another embodiment hereof the blister pack are enclosed in an aluminium sachet of suitable size, composed of aluminium laminated to calendered kraft paper.

In yet another embodiment the fast dispersing dosage form is packed in blister packs formed from aluminium and sealed with aluminium laminated to calendered kraft paper.

In a further embodiment the fast dispersing dosage form is packed in multilamilar blister packs formed from e.g. five layer aluminium laminate and sealed with aluminium laminated to calendered kraft paper.

In yet another embodiment the fast dispersing dosage form is packed in blister packs formed from aluminium laminate and sealed with aluminium laminated to calendered kraft paper in such a way that is difficult for children to open the blister pack e.g. child resistant packs A non-compressed fast dispersing solid dosage form is normally characterized by a low mechanical strength compared to compressed tablets, because of the inherent nature of such a non-compressed dosage form. This may result in the release of residual particles containing the allergen on removal from the blister pocket and during handling of the dosage form by the patient. In most situations this is of no or mainly cosmetic importance. However, this is especially detrimental when the active ingredient is an allergen, because low amounts allergen can elicit an allergic reaction in a disposed person or sensitise. Normally exposure is in the range of 10 μg/year to major allergen protein accumulated for e.g. pollen allergens or dust mite allergens, which are adequate to give sensitisation or symptoms.

Upon handling the solid dosage forms, allergens may come in contact with target organs like the airways or the eye and elicit a response in an allergic person. One dosage form may contain as much allergen as a person is exposed to in the course of one year or more depending upon the nature of the exposure. It is possible to induce eye symptoms in allergic patients using a conjunctival allergen challenge. Based on such challenge studies it can be estimated how much allergen extract is needed to induce conjunctival symptoms. In a population of patients with severe grass-pollen induced hayfever, the lowest dose of grass pollen extract causing conjunctival symptoms was proposed to be 3000 SQ-U/ml×0.05 ml=150 SQ-U (median value) (S. R. Durham, S. M. Walker, E. M. Varga, M. R. Jacobson, F. O'Brien, W. Noble, S. J. Till, Q. A. Hamid, and K. T. Nouri-Aria. Long-term clinical efficacy of grass-pollen immunotherapy. N.Engl.J.Med. 341 (7):468-475, 1999).

Thus, in one embodiment of the dosage form of the invention less than 500 SQ-U is released from each solid dosage form during manual handling, more preferably less than 250 SQ-U, most preferably less than 150 SQ-U.

In order to ensure that allergen containing residues from the solid dosage form is not released to the environment upon opening the blister pack, it is important that the friability of the dosage form is as low as possible without jeopardising the allergen release from the dosage form following oral administration.

In a preferred embodiment of the present invention the residual content of dust in the blister pack after removing the dosage form do not exceed 2% of total allergen content, more preferred 0.5% of total allergen content of a solid dosage form and more preferably 0.2% of total allergen content of a solid dosage form and most preferably 0.1% of total allergen content of a solid dosage form.

Normally friability testing of compressed tablets is preformed as set out in the Pharmacopeia E.P. 2.9.7 and USP <1216>, wherein loss of weight is assessed as a parameter of an intact dosage form. Accordingly, the intactness of the current dosage form may be assessed by visual inspection and measurement of tablet weight upon having been subject to such a method. Alternatively, due to the low weight of dosage forms according to the invention the weighing can be replaced with an immune assay specific for the allergen in question.

The use of a modified friability test has been found to be a useful tool in assessing which compositions are most stable with respect to robustness and mechanical strength. In an embodiment the friability of said solid dosage form measured as the amount of allergen released is less than 500 SQ-U per solid dosage form, more preferably less than 250 SQ-U per solid dosage form, most preferably less than 150 SQ-U per solid dosage form in any suitable friability test that exerts a sufficient external force on the compositions to be tested. In a more preferred embodiment the friability measured as the amount of allergen released is less than 500 SQ-U per solid dosage form, more preferably less than 250 SQ-U per solid dosage form, most preferably less than 150 SQ-U per solid dosage form in a friability test performed according to the Pharmacopeia. In an even more preferred embodiment the friability measured as the amount of allergen released is less than 500 SQ-U per solid dosage form, more preferably less than 250 SQ-U per solid dosage form, most preferably less than 150 SQ-U per solid dosage form in an assay comprising the following steps;
a) placing individual units of solid dosage form contained in sealed blister pack unit in an equipment suitable for friability measurements
b) moving it for an appropriate time and at an appropriate velocity
c) removing the sealed solid dosage form unit
d) opening the sealed solid dosage form unit and emptying the unit content in a container/placing the fast dispersing dosage form unit and any residues in a container
e) removing the solid dosage form unit from the container leaving any loose residuals in said container
f) performing an allergen specific assay on said residues determining the allergen content in said residues
g) optionally calculating the percentage allergen content in said residues of the total allergen content of the solid dosage form unit.

In a preferred embodiment of the friability method the units are rotated 100 turns at 25±1 rpm and the allergen content is determined by an ELISA assay.

Furthermore, the oral dosage form preferably has an appealing appearance. Hence, as a part of the quality control the fast dispersing solid dosage forms according to the invention are preferably subjected to visual inspection, e.g for parameters such as colour, shape, irregularities and defects.

In order to ensure optimum compliance of the patient, it is preferred that the patients perceive the dosage form as being pleasant when it is placed in the mouth and allowed to disintegrate. Thus, the dosage form is preferably also tested for mouth feel.

As allergens are very bio-potent for the allergic person i.e. even small amount may trigger a response, it is preferred that the content of allergen is uniform during treatment e.g. to ensure that a response pattern experienced for a patient may be reproduced when the same dose is administered. Preferably the variation of content of allergen of units within a blister pack is within ±10%, preferably within ±7%, most preferable within ±5% compared to the dose set.

A blister pack may contain any conceivable number of fast dispersing solid dosage forms. In preferred embodiment the blister pack contains 1-100 solid dosage forms and more preferably 5-35 solid dosage forms. The blister packs may further be packed in appropriate containers in accordance with any particular dose regime that is required to desensitise a patient.

Furthermore, the present invention relates to a method of producing a fast dispersing non-compressed solid dosage form according to claim 1, comprising the steps of: preparing an aqueous dosing solution of the pharmaceutically active substance and maltodextrin and optionally one or more further matrix forming agents and suitable excipients, introducing the solution into depressions of a multilayer laminated blister sheet, subjecting the loaded sheet to freezing and freeze-drying using standard conditions of shelf temperature and chamber pressure.

Moreover, the present invention relates to a method of obtaining a fast dispersing non-compressed allergen vaccine solid dosage form suitable for oromucosal administration comprising
1) producing a fast dispersing, non-compressed solid allergen vaccine dosage form
2) measuring the friability of said dosage form in an assay comprising the steps of
a) placing a solid dosage form contained in a sealed blister pack unit in an equipment suitable for friability measurements
b) moving it for an appropriate time and at an appropriate velocity
c) removing the sealed solid dosage form unit
d) opening the sealed solid dosage form unit and emptying the unit in a container/placing the fast dispersing dosage form unit in a container
e) removing the solid dosage form unit from the container leaving any loose residues in said container
f) performing an immunochemical allergen specific assay on said residues detecting the amount of allergen content in said residues g) calculating the percentage of allergen content in said residues in comparison to total allergen content of the solid dosage form unit
h) detecting whether the dosage form fulfills the requirements for low friability.
3) repeating 1) and 2) until the requirements for the dosage form is fulfilled.

Treatment

The fast dispersing solid dosage form according to the invention can be prepared by a sublimation process according to the process disclosed in U.S. Pat. No. 4,371,516. Accordingly, a solidified solution of the allergen and the matrix forming excipients is subjected to sublimation. The sublimation process is preferably carried out by freeze-drying the solution. The solution is contained in a depression of the blister pack during the freeze-drying step to produce a solid form in any desired shape. The blister pack can be cooled using liquid nitrogen or solid carbon dioxide. After the freezing step the frozen solution in the blister pack is subjected to reduced pressure and, if desired, controlled application of heat to aid the sublimation of the solvent.

Clinical allergy manifestation and symptoms are several and may vary depending on the sensitized individual and the allergy inflicted. Common are symptoms like edema, itching, redness and running of the eyes and nose (rhinitisconjunctivitis) and symptoms from upper and lower airway like wheezing, coughing, shortness of breath, skin condition like eczema, urticaria and itching. Other symptoms like fatigue are also experienced. Symptomatic treatment aims at reducing or affecting severity of the symptoms or reducing the need for other drugs given in parallel. Symptomatic drugs include antihistamines like H1 and H2 receptor antagonists, intranasal and systemic corticosteroids, non-steroid anti-inflammatory drugs, nasal decongrdtans like adrenoceptor agonists. Treatment and relief of one or more allergic symptoms or the reduction of the need for other medication is a further object of this invention.

Thus, the present invention relates to a method of preventing or treating a disease comprising oromucosal administration of an effective amount of a dosage form according to the invention.

More specifically, the present invention relates to a method for preventing or treating allergy or alleviating symptoms of allergy comprising oromucosal administration of an effective amount of an allergen vaccine dosage form according to the invention.

The present invention also relates to a pharmaceutically active substance for the manufacture of a fast dispersing non-compressed solid dosage form according to the invention.

More specifically, the present invention relates to an allergen for the manufacture of a fast dispersing non-compressed allergen vaccine solid dosage form according to the invention.

Further, the present invention relates to a fast dispersing non-compressed solid dosage form according to the invention for oromucosal prevention or treatment of a disease.

More specifically, the present invention relates to a fast dispersing non-compressed allergen vaccine solid dosage form according to the invention for oromucosal prevention or treatment of allergy or alleviation of allergic symptoms.

Also, the present invention relates to the use of a pharmaceutically active substance for the manufacture of a fast dispersing or non-compressed solid dosage form according to claim 1 for oromucosal prevention or treatment of a disease.

More specifically, the present invention relates to the use of an allergen for the manufacture of a fast dispersing or non-compressed allergen vaccine solid dosage form according to claim 1 for oromucosal prevention or treatment of allergy or alleviation of allergic symptoms.

Sublingual immunotherapy can be regarded as a way of inducing tolerance inducing mucosal vaccination. The mucosa of the mouth is rich in dendritic cells with a strong potential for antigen presentation. The dendritic cells are believed to process the allergens and then migrate to the local lymph nodes where they present allergen derived peptides to allergen specific T cells. During sublingual immunotherapy this dendritic cell—T cell interaction is believed to induce T cells with regulatory potential or to increase the ratio of allergen specific Th1 cells to allergen specific Th2 cells. A number of immunological parameters monitored during the allergy vaccination may be suitable markers for effects or efficacy of the treatment, alone or in combination respectively. These include systemic and mucosal antibody responses e.g. specific IgA, IgG and IgE antibodies; cytokine levels e.g. INFgamma, IL-2, IL-4, IL-5, IL-10, IL-12 and TNF alpha in blood or mucosal secretions; activation, chemotaxis, proliferation, signalling, cytokine production and other responses of regulatory T-cells, Th1 cells, TH2 cells, CD8 cells, other T cell subsets or B-cells or NK cells, and cell surface marker expression such as CD (cluster of differentiation) markers e.g. CD4, CD8, CD23, CD25, CD62L, CLA, beta7, CCR9, CD69, CD45RO, CCR3, CXCR5, effector cell function such as total histamine content of basophils; eosinophil, basophil, lymphocyte, monocyte numbers in blood, tissue and secretions; eosinophil, basophil, lymphocyte, monocyte mediator release, cytokine production, activation, chemotaxis, proliferation, signalling and other responses.

In a preferred embodiment the dosage form according to the present invention has a profile where one or more of the following immunological changes can be found; an increased allergen specific IgG response, an increased allergen specific IgA response, reduced allergen specific IgE response, few local side effects; reduced allergen specific effector responses of eosinophils, basophils, lymphocytes and/or monocytes; induction of T cells with regulatory potential, increased ratio of allergen specific Th1 cells to allergen specific Th2 cells, induction of other cells with regulatory potential, reduced allergen specific Th2 response.

Allergy is also a known disease in animals especially domestic and companionship animals. It is known in the art that they develop allergies toward numerous allergen sources including grass, house dust mites, and parasites. Hematopgagus, i.e. bloodsucking insect infestation is known to lead to a hypersensitive response called flea allergic dermatitis (FAD). In a preferred embodiment of the current invention allergens for animal vaccines include allergens originating or transferred from parasites like ectoparasites (e.g. fleas, ticks, mosqistos, flies), parasitic helminth venom (like hearth worm e.g. Dirotilaria or onchocerciasis e.g. Onchocerca) and house dust mite. More preferred are saliva allergens from fleas like Ctenocephalides e.g. *C. canis* and *C. felis*, hard ticks likes Ixodes, Arnblyomma, soft ticks like Ornithodoros and from midges like Culicoides.

Dosage Forms Containing Microcapsules

Peyer's patches are aggregates of lymphoid nodules located in the wall of the small intestine, large intestine and appendix and are an important part of body's defense against the adherence and penetration of infection agents and other substances foreign to the body. Peyer's patches are also known as folliculi lymphatic aggregate. Similar folliculi lymphatic aggregati can be found in the respiratory tract, the rectum, the nasal cavity, the oral cavity, the pharynx, the genitourinary tract, large intestine and other mucosal tissues of the body. The said tissues may in general be referred to as mucosally-associated lymphoid tissues (MALT).

It has been shown that pharmaceutically active substances formulated as microcapsules having a proper size and suitable physico-chemical properties may be effectively taken up by Peyer's patches and MALT.

Accordingly, an additional aspect of the present invention relates to a dosage form, wherein at least a part of the active substance is present in the form of microcapsules embedded in the matrix, the microcapsules comprising a first encapsulating agent and the active substance. Without being bound by theory it is believed that for a number of active substances, in particular allergens, it is possible to obtain the intended therapeutic effect by microcapsules, which may be taken up by the MALT or allowed to elicit its effects via the MALT. In a preferred embodiment of the invention, the active substance is present in the matrix both in form of microcapsules and in the form of molecules in direct contact with the matrix. It is believed that in this embodiment the active substance is taken up and/or allowed to elicit its effects by two different mechanisms, i.e. both via the MALT and via immunosystem stimulation elicited by free allergens, and hence an enhanced therapeutic effect is obtained as compared to the situation, where the active substance is formulated either as microcapsules or in direct combination with the matrix.

In addition to enhanced therapeutic effects, the use of microcapsules involves the advantage of protecting the pharmaceutical active substance from degradation, both during production and storage of the dosage forms, and in the process of administration of the active substance to the patient. As described in more detail elsewhere in this application, this is particularly important, when the active substance is an allergen. The use of microencapsulation to protect sensitive bioactive substances from degradation has become well-known. Typically, a bioactive substance is encapsulated within any of a number of protective wall materials, usually polymeric in nature. The agent to be encapsulated can be coated with a single wall of polymeric material (microcapsules), or can be homogeneously dispersed within a polymeric matrix (microspheres). (Hereafter, the term microcapsules refers to both microcapsules and microspheres and the terms "encapsulation" and "microencapsulation" should be construed accordingly). The amount of substance inside the microcapsule can be varied as desired, ranging from either a small amount to as high as 95% or more of the microcapsule composition. The diameter of the microcapsule is preferably less than 20 μm, more preferably less than 15 μm, more preferably less than 10 μm and most preferably between 1 and 10 μm.

Furthermore, the use of microcapsules involves the advantage of preventing the release of the active substance from the dosage form. As described in more detail elsewhere in this application, this is particularly important, when the active substance is an allergen.

The encapsulating agent may be any biodegradable agent, preferably a polymeric agent. Preferably, the first encapsulating agent is selected from the group consisting of poly-lactide, poly-lactid-poly(ethylene glycol), poly(DL-lactide-co-glycolide), poly(glycolide), copolyoxalates, polycaprolactone, poly(lactide-co-caprolactone), poly(esteramides, polyorthoesters and poly(8-hydroxybutyric acid), and polyanhydrides, most preferably poly(DL-lactide-co-glycolide). Other examples of encapsulating agents are poly(butyl-2-cyanoacrylate), poly(3-hydroxybutyrate) and polyanhydride copolymers of fumaric and sebacic acid, poly(FA: SA). Also, suitable encapsulating agents for use according to the present invention include those derived from animal or vegetable proteins, such as gelatines, dextrins and soy, wheat and psyllium seed proteins; gums such as acacia, guar, agar and xanthan; polysaccharides; starch and modified starch, alignates; carboxymethylcellulose; carrageenans; dextrans; pectins; synthetic polymers such as polyvinylpyrrolidone; and polypeptide/protein or polysaccharide complexes such as gelatine-acacia complexes. In one embodiment of the invention two or more encapsulating agents are used. Preferably, the encapsulating agent is selected so as to make the microparticles hydrophobic. It is believed that hydrophobic microparticles are more easily taken up by the MALT or allowed to elicit its effects via the MALT.

In one preferred embodiment of the invention, the microcapsule-containing dosage form is formulated as a tablet, i.e. a coherent dosage form unit. In another preferred embodiment, the microparticle-containing dosage form is formulated as a granular composition, e.g. a granular composition suitable for preparing a compressed tablet. Also, the dosage form of the invention, wherein the pharmaceutically active substance is present in direct combination with the matrix forming agent, may be formulated as a granular composition, e.g. a granular composition suitable for preparing a compressed tablet.

The present invention further relates to a compressed tablet comprising the granular composition of the invention.

Furthermore, the present invention relates to an aqueous dosing solution for preparing a fast-dispersing solid composition suitable for oromucosal administration of a pharmaceutically active substance, the dosing solution comprising
(a) a first matrix forming agent in the form of maltodextrin having a dextrose equivalent (DE) of between 1 and 20, and
(b) microcapsules comprising a first encapsulating matrix forming agent and the active substance.

Finally, the present invention relates to a method of preparing the dosage form according to the invention comprising the steps of:
preparing microcapsules comprising a first encapsulating matrix forming agent and a pharmaceutically active substance,
preparing an aqueous dosing solution of the microcapsules and maltodextrin and optionally one or more further matrix forming agents and suitable excipients,
spray-freezing the dosing solution to produce primary granules, and
freeze-drying the primary granules to produce secondary granules.

DEFINITIONS

The term "maltodextrin" means a partly hydrolysed starch having a dextrose equivalent (DE) of between 1 and 20.

The term "fast dispersing dosage form" refers to dosage forms which disintegrate in less than about 90 seconds, preferably in less than 60 seconds, preferably in less than 30 seconds, more preferably in less than 20, even more preferably in less than 10 seconds in the oral cavity, even more preferred in less than 5, most preferably in less than about 2 seconds of being placed in the oral cavity.

The term "stable" refers to dosage forms where the loss in allergen content of at least one major allergen according to the method described in Example 1 is less than 50% of the initial content.

The term "low friability" refers to the amount of residual material that is lost from the dosage form when it is subjected to an external force. The solid dosage form has a sufficient friability and robustness to be transported, stored and handled if the residual material lost contains less than 500 SQ-units per solid dosage form, more preferably less than 250 SQ-units per solid dosage form, most preferably less than 150 SQ-U per solid dosage form of the total allergenic content of the dose. For the purpose of the present invention, the friability may be measured by a method according to the present invention or may be measured by a modified method according to the European Pharmacopeia.

The term "non-compressed" refers to a solid dosage form, which is manufactured by removal of a liquid from a solidified system comprising matrix forming agents, active ingredient and other suitable ingredients resulting in a solid matrix.

The term "solid dosage form" refers to a dosage form, which is not a liquid, e.g. a tablet or a granular composition, when it is administered in the oral cavity.

"Tensile strength σ" is calculated according to the following equation $$\sigma = 3Wa \times 9.8 \, Nmm - 2/2 \, d2 \, b$$

where w=Peak load to fracture (kgF)
 a=distance between supports
 d=thickness of the fast dispersing solid dosage form (mm)
 b=diameter of the fast dispersing solid dosage form (mm)

"Peak load to fracture" means the peak force required to fracture a unit in a three point bend test using an appropriate instrument (e.g. CT5, Engineering Systems, 1 Loach Court, Radford Bridge Road, Nottingham NG8 1NA).

The term "oromucosal" refers to a dosage form that is placed under the tongue or anywhere else in the oral cavity that allows the active ingredient to come in contact with the mucosa of the oral cavity or the pharynx of the patient.

The term "mono-saccharide" refers to any saccharide containing six carbons, whether in the form of a ring or a linear molecule. The term "di-saccharide" refers to any saccharide comprising any combination of two mono-saccharides. The term "tri-saccharide" refers to any saccharide comprising any combination of three mono-saccharides.

The "dosing solution" means the non-solid mixture of the solvent, the matrix forming agents, the active substance, and other optional excipients subjected to solidification.

The term "allergen" refers to any naturally occurring protein or mixtures of proteins that have been reported to induce allergic, i.e. IgE mediated reactions upon their repeated exposure to an individual. Examples of naturally occurring allergens include pollen allergens (tree-, weed and herb- and grass pollen allergens), mite allergens (from e.g. house dust mites and storage mites), insect allergens (inhalant, saliva- and venom origin allergens), animal allergens from e.g. saliva, hair and dandruff from e.g. dog, cat, horse, rat, mouse, etc., fungis allergens and food allergens. The allergen may be used in the form of an allergen extract, a purified allergen, a modified allergen or a recombinant allergen or a recombinant mutant allergen, any allergen fragment above 30 amino acids or any combination thereof.

SQ-unit: The SQ-unit is determined in accordance with ALK-Abelló A/S's "SQ biopotency" standardisation method, where 100.000 SQ units equal the standard subcutaneous maintenance dose. Normally 1 mg extracts contains between 100000 and 1000000 SQ-unit depending on the allergen source from which they originate and the manufacturing process used. The precise allergen amount can be determined by means of immunoassay i.e. total major allergen content and total allergen activity. In this field of expertise, there is no international accepted standardisation method. Hence, if extracts of other origins are used, they need to be standardised against an ALK-Abello A/S extract, which is a well-known procedure for the person skilled in the art. The subject matter is dealt with in "Allergenic extracts", H. Ipsen et al, chapter 20 in Allergy, principle and practise (Ed. S. Manning) 1993, Mosby-Year Book, St. Louis and Løwenstein H. (1980) Arb Paul Ehrlich Inst 75:122.

"Uniformity of content" shall mean the variation of the doses unit from the stated dose.

"Water content" shall mean the content of residual water in a solid dosage unit determined quantitatively using a Karl Fischer titration principle. This method is based on the principle that a given amount of I2 leads to a transformation of an equivalent amount of water (European Pharmacopoïea 2.5.12)

As used herein "Water activity aw" is the effective water in a sample. Water activity measurements are carried out using methods known to the person skilled in the art, for example chilled mirror dew point technology, relative humidity with sensors that change electrical resistance or capacitance or using a lithium chloride electrode:

aw can be calculated according to the following equation $$aw = p/ps = ERH \, (\%)/100$$

where
p=partial pressure of water vapor at the surface of the product
ps=saturation pressure, or the partial pressure of water vapor above pure water at the product temperature.
ERH=equilibrium relative humidity.

EXAMPLES

Abbreviations

API: Active Protein Ingredient
ELISA: Enzyme Linked Immuno Sorbent Assay
DDT: Dithiothreitol
HRP: Horse Radish Peroxidase
LIA: Magic Lite specific IgE assay
LITE-reagent: Luminescence labbelled anti-gE
PMP: Para Magnetic Particles
SDS-PAGE: Sodium dodecyl sulphate poly-acryl amide gel electrophoresis
TMB:Tertametylbenzidine.

Example 1

Grass Extract

Grass pollen extract was prepared according to the method describes in Ipsen and Løwensten (1983) Jour. Allergy. Clin. Immunol. 72:2, page 150-159. In short grass pollen was extracted in ammonium hydrogen carbonate, for 20 hours at 5° C. Particulate matter was removed by centrifugation and the supernatant was dialysed against water (3 times), lyophilised and stored cold until reconstitution.

Solid Dosage:
Manufacturing Process:
1. MQ water is added to a beaker with a magnet stirrer.
2. Mannitol and sorbitol, if any, is added and dissolved under stirring.
3. Maltodextrin and PEG, if any, is added and dissolved under stirring.
4. Allergen extract, if any, is added.
5. If allergen is present, pH is adjusted to pH=7-8 using hydrochloric acid (2N) or sodium hydroxide (2N).
6. 250 μl of the solution was dosed into pre-formed blister packs. The solutions were dosed under ambient temperature conditions.

7. After dosing, the filled blister packs were freezed at −80° C. The units were freeze-dried using standard conditions of shelf temperature and chamber pressure.

Short Descriptions of Analytical Methods:

Visual inspection: All units were subjected to visual inspection e.g colour, shape, irregularities and defects to ensure acceptable appearance.

Disintegration: The test was performed as described in the current European Pharmacopoeia or the current USP.

Water content: The residual water was determined using a Karl Fischer titration principle. The method gives a quantitative determination of the water content in a sample based on the principle that a given amount of $I_2$ leads to transformation of an equivalent amount of $H_2O$.

Composition

| Code | Mannitol | Maltodextrin | Sorbitol | Allergen extract |
|------|----------|--------------|----------|------------------|
| A | 3 w/w-% | 5 w/w-% | — | 0.002 w/w-% |
| B | 3 w/w-% | 5 w/w-% | 0.1 w/w-% | 0.002 w/w-% |
| C | 3 w/w-% | 5 w/w-% | 1 w/w-% | 0.002 w/w-% |

Results of analytical tests

| Code | Water content | Disintegration | Visual inspection |
|------|---------------|----------------|-------------------|
| A | 4.5% | 1 sec. | Very difficult to remove solid unit in one piece from blister pack |
| B | 4.4% | 1 sec. | Very difficult to remove solid unit in one piece from blister pack |
| B | 3.8% | 1 sec. | Very difficult to remove solid unit in one piece from blister pack |

* The amount of API dependent on the reconstitution factor of the specific batch API.

It has been shown possible to produce freeze-dried solid dosage forms with various contents of mannitol, maltodextrin, allergen extract with and without sorbitol. The dosage forms all had a disintegration time of 1 sec.

Example 2

| Code | Mannitol | Maltodextrin | Sorbitol |
|------|----------|--------------|----------|
| A | 3 w/w-% | 5 w/w-% | — |
| B | 3 w/w-% | 5 w/w-% | 0.1 w/w-% |
| C | 3 w/w-% | 5 w/w-% | 1 w/w-% |

Results of analytical tests

| Code | Water content | Disintegration | Visual inspection |
|------|---------------|----------------|-------------------|
| A | 4.6% | n.m. | Impossible to remove solid unit in one piece from blister pack |
| B | 4.6% | n.m. | Impossible to remove solid unit in one piece from blister pack |
| C | n.m. | n.m. | Impossible to remove solid unit from blister pack |

* It was only possible to remove 3 solid units from the blister pack, which is why the test for disintegrations is based on only 3 units.

It has been shown possible to produce freeze-dried solid dosage forms with various contents of mannitol, maltodextrin and/or sorbitol.

Example 3

| Code | Mannitol | Maltodextrin | Sorbitol | PEG 6000 |
|------|----------|--------------|----------|----------|
| A | 5 w/w-% | 10 w/w-% | 0.1 w/w-% | — |
| B | 10 w/w-% | 20 w/w-% | 0.1 w/w-% | — |
| C | 10 w/w-% | 20 w/w-% | — | — |
| D | 5 w/w-% | — | 0.1 w/w-% | 5 w/w-% |
| E | 10 w/w-% | — | 0.1 w/w-% | 10 w/w-% |
| F | 10 w/w-% | — | — | 10 w/w-% |

Results of analytical tests

| Code | Water content | Disintegration | Visual inspection |
|------|---------------|----------------|-------------------|
| A | n.m. | n.m. | Impossible to remove solid unit in one piece from blister pack |
| B | 5.1% | 3 sec. | Very difficult to remove solid unit in one piece from blister pack |
| C | n.m. | n.m. | Very difficult to remove solid unit in one piece from blister pack |
| D | n.m. | n.m. | Impossible to remove solid unit in one piece from blister pack |
| E | n.m. | n.m. | Impossible to remove solid unit in one piece from blister pack |
| F | n.m. | n.m. | Impossible to remove solid unit in one piece from blister pack |

It has been shown possible to produce freeze-dried solid dosage forms with various contents of mannitol and/or maltodextrin and/or sorbitol and/or PEG. A dosage form comprising mannitol, maltodextrin and sorbitol had a disintegration time of 3 sec.

Example 4

| Code | Mannitol | Maltodextrin | Sorbitol | PEG 6000 |
|------|----------|--------------|----------|----------|
| A | 5 w/w-% | 20 w/w-% | 0.1 w/w-% | — |
| B | 5 w/w-% | 20 w/w-% | 0.1 w/w-% | 3 w/w-% |
| C | 5 w/w-% | 35 w/w-% | 0.1 w/w-% | — |
| D | 5 w/w-% | 35 w/w-% | 0.1 w/w-% | 3 w/w-% |
| E | 5 w/w-% | 35 w/w-% | 0.2 w/w-% | — |
| F | 5 w/w-% | 35 w/w-% | 0.2 w/w-% | 3 w/w-% |

Results of analytical tests

| Code | Water content | Disintegration | Appearance |
|------|---------------|----------------|------------|
| A | n.m. | 5 sec. | Possible to remove solid unit in one piece from blister pack |
| B | n.m. | 2 sec. | Impossible to remove solid unit in one piece from blister pack |
| C | n.m. | 81 sec. | Possible to remove solid unit in one piece from blister pack |
| D | n.m. | 58 sec. | Possible to remove solid unit in one piece from blister pack |
| E | n.m. | 95 sec. | Very difficult to remove solid unit in one piece from blister pack |
| F | n.m. | 83 sec. | Very difficult to remove solid unit in one piece from blister pack |

It has been shown possible to produce freeze-dried solid dosage forms with various contents of mannitol and/or maltodextrin and/or sorbitol and/or PEG. A dosage form comprising mannitol, maltodextrin and sorbitol had a disintegration time of 3 sec.

Example 5

This example relates to the preparation of a granular composition of granules having a matrix composed of maltodextrin, mannitol and sorbitol, wherein the matrix comprises microencapsulated allergen (MEA), and to the preparation of compressed tablets from the granular composition.
Materials
Encapulating agent: Poly-D,L-Lactide-Glycolide (DL-PLG) (60/40) with an MW of 40,000 g/mol, obtained from Birmingham Polymers in the USA.
Active substance: Phi p extract in MEA-particles.
Mannitol: Ph. Eur. <559>, No. 281048 from Unikem.
Sorbitol: Ph. Eur. <435>, No. 340927 from Nomeco.
Maltodextrin: NF 18, type CPUR01915 (18 DE) from Cerestar.
Talcum: Ph. Eur. <438>, No. 297911 from Unikem.
Magnesium sterate: Ph. Eur. <229>, No. 280560 from Unikem.
Test Methods for Compressed Tablets
Resistance to Crushing
The tablet is placed horizontally on a support against a first vertical plate. A piston fitted with a second vertical plate at its distal end, the two plates being disposed parallel, is moved against the tablet, and the pressure in N applied at the time of crushing of the tablet is measured.
Friability
20 tablets are dusted off and weighed and then placed in a cylinder fitted with internal ribs. The cylinder is rotated at 25 rpm for a selected period of time, removed from the cylinder, dusted off and weighed. The difference in initial and final weight is calculated in percent and expresses the friability.
Preparation of MEA
1. Homogenisation.
DL-PLG is dissolved in ethyl acetate (30 w/w %), and the allergen extract is dissolved in water (13 w/w %). The two solutions are mixed and homogenised to form an oil/water two-phase emulsion.
2. Emulsifying the oil/water emulsion in an aqueous medium.
The oil/water emulsion is mixed with a 2 w/w % aqueous solution of PVA, which is saturated with ethyl acetate and buffered to pH=6.8 using sodium phosphate and hydrochloric acid, and emulsified to form a water/oil/water emulsion. The water/oil/water emulsion is passed through an emulsion sieve in the emulsifying apparatus to form MEA-microcapsules.
3. Extraction of ethyl acetate/PVA.
In order to cure the MEA-microcapsules, ethyl acetate and PVA are extracted. For the first 10 minutes of the extraction, the temperature is maintained at 22° C., after which the temperature is lowered to 12° C.
4. Up-concentration by means of centrifugation.
The suspension formed in step 3 is subjected to centrifugation.
5. Re-suspension and spray drying.
After centrifugation the microcapsules are re-suspended in water (1800 ml/25 g) and subjected to spray drying to form the finished microcapsules.
Preparation of Granular Composition
MEA is suspended in distilled water and mannitol, maltodextrin and sorbitol are added, and the suspension is stirred. The resulting mixture is sprayed into a chamber filled with liquid nitrogen, wherein the droplets freeze immediately. During the spray-freezing, a portion of the droplets will freeze together, and therefore the frozen particulate composition is optionally subjected to crushing. The crushed ice particles are sieved and freeze dried and sieved again to obtain the finished granules.
Preparation of Tablets
The tablets were produced using a "Comprex II" tabletting apparatus.
Composition

| | Material | MEA w/w % | Mannitol w/w % | Malto-dextrin w/w % | Sorbitol w/w % | Water w/w % |
|---|---|---|---|---|---|---|
| A | MEA | 100.0 | | | | |
| | Dosing sol. | 6.7 | 6.7 | 26.7 | 6.7 | 53.3 |
| | Granules | 14.3 | 14.3 | 57.2 | 14.3 | |
| B | MEA | 100 | | | | |
| | Dosing sol. | 16.5 | 8.3 | 23.3 | 1.6 | 50.2 |
| | Granules | 33.2 | 16.7 | 46.8 | 3.3 | |
| C | MEA | 100.0 | | | | |
| | Dosing sol. | 16.5 | 8.3 | 23.3 | 1.6 | 50.2 |
| | Granules | 33.2 | 16.7 | 46.8 | 3.3 | |
| D | MEA | 100.0 | | | | |
| | Dosing sol. | 10.9 | 9.5 | 11.5 | 0.0 | 68.1 |
| | Granules | 34.1 | 29.8 | 36.1 | 0.0 | |
| E | MEA | 100.0 | | | | |
| | Dosing sol. | 11.6 | 9.0 | 11.3 | 0.5 | 67.6 |
| | Granules | 35.8 | 27.8 | 35.0 | 1.4 | |
| F | MEA | 100.0 | | | | |
| | Dosing sol. | 11.3 | 9.0 | 11.3 | 0.7 | 67.7 |
| | Granules | 34.9 | 27.9 | 35.1 | 2.1 | |

Results

| | Material | 1-5 μm % | 5-10 μm % | <10 μm % | STD <10 μm % | Resistance to crushing (N) | Friability |
|---|---|---|---|---|---|---|---|
| A | MEA | 53.8 | 32.3 | 91.2 | 0.1 | | |
| | Dosing sol. | | | | | | |
| | Granules | 57.4 | 30.6 | 93.0 | 0.1 | | |
| | Tab 15 min. | 55.2 | 29.3 | 88.7 | 0.8 | | |
| | Tab 30 min. | 54.1 | 29.1 | 87.2 | 1.7 | | |
| B | MEA | 41.7 | 33.4 | 79.0 | 1.0 | | |
| | Dosing sol. | | | | | | |
| | Granules | 57.6 | 31.4 | 92.6 | 0.1 | | |
| | Tab 15 min. | 57.5 | 28.8 | 90.7 | 0.9 | | |
| | Tab 30 min. | 58.4 | 27.5 | 90.1 | 1.0 | | |

-continued

|   | Material | 1-5 μm % | 5-10 μm % | <10 μm % | STD <10 μm % | Resistance to crushing (N) | Friability |
|---|---|---|---|---|---|---|---|
| C** | MEA | 41.7 | 33.4 | 79.0 | 1.0 | | |
|   | Dosing sol. | | | | | | |
|   | Granules | 39.7 | 34.6 | 78.1 | 0.0 | | |
|   | Tab 15 min. | | | | | | |
|   | Tab 30 min. | 41.0 | 32.7 | 77.2 | 0.5 | 43.7 | |
| D | MEA | 49.9 | 40.6 | 94.4 | 2.8 | | |
|   | Dosing sol. | | | | | | |
|   | Granules | 44.0 | 36.8 | 84.2 | 0.3 | | |
|   | Tab' 30 min. | 53.4 | 31.1 | 87.9 | 0.4 | 20.1 | |
|   | Tab" 30 min. | 50.6 | 31.8 | 85.8 | 0.5 | 39.8 | |
| E** | MEA | 35.5 | 30.8 | 70.6 | 0.1 | | |
|   | Dosing sol. | | | | | | |
|   | Granules | 36.9 | 30.3 | 71.6 | 0.5 | | |
|   | Tab 15 min. | 38.1 | 25.7 | 66.8 | 1.5 | | |
|   | Granules* | 28.7 | 25.1 | 57.0 | 2.5 | | |
|   | Tab*. | 27.5 | 22.5 | 52.2 | 2.4 | 76.1 | |
| F** | MEA | 35.5 | 30.8 | 70.6 | 0.1 | | |
|   | Dosing sol. | | | | | | |
|   | Granules | 36.0 | 30.6 | 70.7 | 0.1 | | |
|   | Tab 30 min. | 32.0 | 24.1 | 59.1 | 1.1 | 60.8 | Positive |
|   | Granules* | 28.7 | 25.1 | 57.0 | 0.2 | | |
|   | Tab* 30 min. | 17.4 | 16.5 | 35.6 | 4.0 | 31.9 | Positive |

*0.5% magnesium stearate and 4.5% talcum added as lubricants.
**Crushing of granules to reduce size
'Tablets compressed at low pressure
"Tablets compressed at high pressure A number of microcapsule-containing granular compositions and compressed tablets with different compositions have been prepared. The compressed tablets all disintegrated quickly, which means that the granular composition is easily dispersible. As will appear from the results of the above table, the particle size distribution of MEA, the granular composition and the tablet after dissolution were in all cases closely similar. Thus, it may be concluded that by use of the present microcapsule-matrix system, it is possible to prepare a granular composition, which may be used to prepare compressed tablets, wherein the microcapsules are maintained intact. Also, as will appear from the results of resistance to crushing and friability, the matrix composed of mannitol, maltodextrin and sorbitol is strong, and in any event sufficiently strong to resist compression into tablets.

The invention claimed is:

1. A freeze-dried non-compressed fast-dispersing solid dosage form prepared by a freeze-drying process suitable for oromucosal administration of an allergen comprising
    (a) a first matrix forming agent, which is maltodextrin having a dextrose equivalent (DE) of between 1 and 20,
    (b) a second matrix forming agent, which is sorbitol, and
    (c) the allergen,
    wherein the allergen is not present in the form of microcapsules embedded in the matrix;
    wherein said solid dosage form disintegrates in less than about 90 seconds in the oral cavity;
    wherein the matrix is free of polymeric matrix forming agents; and
    wherein said dosage form does not contain cellulose derivatives.

2. A dosage form according to claim 1 comprising one or more further matrix forming agents.

3. A dosage form according to claim 2, wherein the further matrix forming agent is a mono-, di- or tri-saccharide.

4. A dosage form according to claim 2, wherein the further matrix forming agent is mannitol.

5. A dosage form according to claim 1 further comprising polyethylene glycol (PEG).

6. A dosage form according to claim 1 further comprising one or more additional excipients.

7. A dosage form according to claim 6, wherein the excipient is selected from the group consisting of adjuvants, antacids, diluents, enhancers, mucoadhesive agents, flavouring agents, taste masking agents, preservatives, antioxidants, surfactants, viscosity enhancers, coloring agents, pH modifiers and sweeteners.

8. A dosage form according to claim 1, wherein the allergen is selected from the group consisting of tree pollen allergens, grass pollen allergens, mite allergens, insect allergens, venom allergens, animal hair and dandruff allergens and food allergens.

9. A dosage form according to claim 1, wherein the allergen is in the form of an extract, a purified allergen, a modified allergen or a recombinant allergen or a mutant of a recombinant allergen or any combination thereof.

10. A dosage form according to claim 1, wherein the allergen is grass pollen.

11. A dosage form according to claim 1, wherein the allergen is dust mite.

12. A dosage form according to claim 1 wherein the dosage form is for sublingual administration.

13. A method for alleviating symptoms of allergy comprising administering an effective amount of an allergen dosage form according to claim 1 to a patient in need thereof by a oromucosal route.

14. A method of producing a fast dispersing non-compressed solid dosage form according to claim 1, comprising the steps of:
    preparing an aqueous dosing solution of the allergen and maltodextrin and optionally one or more further matrix forming agents and suitable excipients,
    introducing the solution into depressions of a multilayer laminated blister sheet, and subjecting the loaded sheet to freezing and freeze-drying using standard conditions of shelf temperature and chamber pressure.

15. A method of obtaining a fast dispersing non-compressed allergen dosage form suitable for oromucosal administration comprising
   1) producing a fast dispersing, non-compressed solid allergen vaccine dosage form
   2) measuring the friability of said dosage form in an assay comprising the steps of
      a) placing a solid dosage form contained in a sealed blister pack unit in an equipment suitable for friability measurements
      b) moving it for an appropriate time and at an appropriate velocity
      c) removing the sealed solid dosage form unit
      d) opening the sealed solid dosage form unit and emptying the unit in a container/placing the fast dispersing dosage form unit in a container
      e) removing the solid dosage form unit from the container leaving any loose residues in said container
      f) performing an immunochemical allergen specific assay on said residues detecting the amount of allergen content in said residues
      g) calculating the percentage of allergen content in said residues in comparison to total allergen content of the solid dosage form unit
      h) detecting whether the dosage form fulfills the requirements for low friability
   3) repeating 1) and 2) until the requirements for the dosage form is fulfilled.

16. The solid dosage form according to claim 1, wherein the polymeric matrix forming agents are selected from the group consisting of gelatines, starch, and gums.

17. The dosage form according to claim 1, wherein the solid dosage form is made by:
   1) preparing an aqueous dosing solution of the allergen, maltodextrin, and sorbitol and optionally one or more further matrix forming agents and suitable excipients;
   2) introducing the solution into depressions of a multilayer laminated blister sheet, and
   3) subjecting the loaded sheet to freezing and freeze-drying using standard conditions of shelf temperature and chamber pressure.

18. The dosage form according to claim 17, wherein the dosing solution comprises maltodextrin in an amount of 3-40% (w/w).

19. The dosage form according to claim 17, wherein the dosing solution comprises sorbitol in an amount of 0.01-10% (w/w).

20. The dosage form according to claim 17, wherein the dosing solution comprises mannitol in an amount of 1-20% (w/w).

21. The solid dosage form according to claim 1, comprising a further matrix forming agent selected from the group consisting of a mono-, di-, and tri-saccharide and wherein the matrix is free of other matrix forming agents other than maltodextrin, sorbitol, and mono-, di- and tri-saccharides.

22. The solid dosage form according to claim 17, comprising a further matrix forming agent selected from the group consisting of a mono-, di-, and tri-saccharide and wherein the matrix is free of other matrix forming agents other than maltodextrin, sorbitol, and mono-, di- and tri-saccharides.

23. The solid dosage form according to claim 1, wherein said maltodextrin has a dextrose equivalent (DE) of between 1 and 10.

24. A freeze-dried non compressed fast-dispersing solid dosage form for oromucosal administration of an allergen comprising:
   (1) a matrix forming agent consisting of maltodextrin having a dextrose equivalent (DE) of between 1 and 20, sorbitol and mannitol, and
   (2) an allergen,
   wherein dosage form is prepared by freeze-drying of an aqueous dosing solution in which dosing solution maltodextrin is present in an amount of 3 to 33% (w/w) of the dosing solution; sorbitol is present in an amount of 0.01 to 0.1% (w/w) of the dosing solution, and mannitol is present in an amount of 1 to 10% (w/w) of the dosing solution;
   wherein the matrix is free of polymeric matrix forming agents;
      wherein said dosage form does not contain cellulose derivatives;
   wherein the allergen is not present in the form of microcapsules embedded in the matrix; and
   wherein the dosage form disintegrates in less than 90 seconds in the oral cavity.

25. A freeze-dried non-compressed fast-dispersing solid dosage form for oromucosal administration of an allergen comprising:
   (1) a matrix forming agent consisting of maltodextrin having a dextrose equivalent (DC) of between 1 and 20, sorbitol and mannitol, and
   (2) an allergen,
   wherein the dosage form is prepared by freeze-drying of an aqueous dosing solution in which dosing solution maltodextrin is present in an amount of 3 to 35% (w/w) of the dosing solution; sorbitol is present in an amount of 0.01 to 0.1% (w/w) of the dosing solution, and mannitol is present in an amount of 1 to 10% (w/w) of the dosing solution;
   wherein the matrix is free of gelatin, starch and gums; and
   wherein the dosage form disintegrates in less than 90 seconds in the oral cavity.

26. A freeze dried non-compressed fast-dispersing solid dosage form for oromucosal administration of an allergen composing:
   (1) a matrix forming agent consisting of maltodextrin having a dextrose equivalent (DE) of between 1 and 20, sorbitol and mannitol, and
   (2) an allergen,
   wherein the dosage form is prepared by freeze-drying of an aqueous dosing solution in which dosing solution maltodextrin is present in an amount of 3 to 35% (w/w) of the dosing solution; sorbitol is present in an amount of 0.01 to 0.1% (w/w) of the dosing solution, and mannitol is present in an amount of 1 to 10% (w/w) of the dosing solution;
   wherein the dosage form is free of gelatin, starch and gums; and
   wherein the dosage form disintegrates in less than 90 seconds in the oral cavity.

* * * * *